United States Patent [19]
Miledi et al.

[11] Patent Number: 5,627,169
[45] Date of Patent: May 6, 1997

[54] SELECTIVE ANTAGONISTS FOR GABA$_{RHO}$ RECEPTOR

[75] Inventors: Ricardo Miledi, Irvine; Larry E. Overman, Corona del Mar; Yoshinori Murata, Irvine; Richard M. Woodward, Aliso Viejo, all of Calif.

[73] Assignee: The Regents of The University of California, Oakland, Calif.

[21] Appl. No.: 277,735

[22] Filed: Jul. 20, 1994

[51] Int. Cl.$^6$ .......................... C07F 9/58; A61K 31/675
[52] U.S. Cl. ............................................. 514/89; 546/21
[58] Field of Search ................... 546/21; 514/89

[56] References Cited

PUBLICATIONS $^3$H–baclofen and $^3$H–Gaba bind to bicuculline–insensitive GABA$_B$ sites in rat brain Hill and Bowery, Nature, 290:149–152, Mar. 12, 1981.

Expression of mammalian γ–aminobutyric acid receptors with distinct pharmacology in *Xenopus oocytes* Polenzani, et al., Proc. Natl. Acad. Sci. USA, 88:4318–4322, 1991.

Effects of Steroids on γ–Aminobutyric Acid Receptors Expressed in Xenopus Oocytes by Poly(A)$^+$RNA from Mammalian Brain and Retina Woodward, et al., Mol. Pharm. 41:89–103, 1991.

Characterization of Bicuculline/Baclofen–Insensitive γ–Aminobutyric Acid Receptors Expressed in Xenopus Oocytes I. Effects of CI Channel Inhibitors Woodward, et al., Mol. Pharm., 42:165–173, 1992.

Effects of Hexachlorocyclohexanes in γ–Aminobutyric Acid Receptors Expressed in Xenopus Oocytes by RNA from Mammalian Brain and Retina Woodward, et al., Mol. Pharm., 41:1107–1115, 1992.

*Primary Examiner*—Alan L. Rotman
*Attorney, Agent, or Firm*—Fish & Richardson P.C.

[57] ABSTRACT

Novel phosphinic and phosphonic acid derivatives of pyridine, pyrrole and azepine with utility as antagonists of the GABA$_{rho}$ receptor are disclosed. These compounds have utility as modulators of the excitability of the central nervous system as mediated by their ability to specifically act on closed-channel binding sites of GABA$_{rho}$ receptors.

9 Claims, 3 Drawing Sheets

SELECTIVE ANTAGONISTS FOR GABA$_{RHO}$ RECEPTOR

This invention was made with government support under Grant No. MH48358 and HL25854, awarded by the National Institute of Health. The government has certain rights in the invention.

BACKGROUND OF THE INVENTION

1. Field of the Invention

This invention relates to a unique class of compounds which selectively modulate the activity of receptors for the amino acid gamma-aminobutyric acid ("GABA"). Specifically, the modulating compounds act on closed-channel binding sites of GABA$_{rho}$ receptors, but have little effect on GABA$_A$ and GABA$_B$ receptors.

2. Description of Related Art

Gamma-aminobutyric acid, commonly known as GABA, is an amino acid which serves as the major neurotransmitter in the mammalian central nervous system, particularly the brain. In general, neurotransmitters are responsible for regulating the conductance of ions across neuronal membranes. At rest, the neuronal membrane possesses a potential or membrane voltage of approximately −80 mv, the interior being negative with respect to the exterior of the cell. The potential is the result of ion (K$^+$, Na$^+$, Cl$^-$, organic anions) distribution across the semipermeable neuronal membrane. Neurotransmitters are stored in presynaptic vesicles and are released under the influence of neuronal action potentials. For example, when released into the synaptic cleft, an excitatory chemical transmitter such as acetylcholine will cause membrane depolarization (change of potential from −80 mv to −50 mv or less). This effect is mediated by post-synaptic nicotinic receptors which are activated by acetylcholine, resulting in an increase of membrane permeability to Na$^+$ ions. The reduced membrane potential triggers neuronal post-synaptic action potential which influence other neurons.

The profound influence of GABA on the central nervous system is related to the presence of GABA receptors in most of the neurons in the brain. GABA regulates the excitability of individual neurons by regulating the conductance of ions across the neuronal membrane. For example, GABA interacts with its recognition site on GABA receptors and causes a related ion channel to open, facilitating the flow of chloride ions down a concentration gradient of the ion channel into the cell. The influx of chloride ions results in the hyperpolarization of the transmembrane potential, thus rendering the neuron less excitable.

GABA receptors have been implicated in the mediation of anxiety, seizures, cognitive function, addictive disorders such as alcholism, and responses to other stresses on the central nervous system. Thus, ligands which enhance or decrease the conductance of ions across the neuronal membrane stimulated by GABA are potentially of significant value in research and therapeutic applications.

Highly common, or "conventional" receptors for GABA are (1) GABA$_A$, which are ligand gated Cl$^-$ channels, and (2) GABA$_B$, which are channels active in the regulation of presynaptic K$^+$ and post-synaptic Ca$^{2+}$ levels. Recently, a GABA receptor which is pharmacologically distinct from the GABA$_A$ and GABA$_B$ receptors was expressed in Xenopus oocytes by poly (A)$^+$ RNA isolated from mammalian retinal tissue. Called GABA$_{ret}$ or GABA$_{rho}$ (hereafter, GABA$_{rho}$), the expressed receptor responded to GABA binding with production of a Cl$^-$ current, indicating that it, like the GABA$_A$ receptors, responds to GABA by mediating Cl$^-$ currents in neuronal membranes. However, although the response of GABA$_{rho}$ is inhibited by certain Cl$^-$ channel inhibitors which also act on GABA$_A$. The GABA$_{rho}$ receptors are insensitive to both the GABA$_A$ antagonist bicuculline ("BIC") and the GABA$_B$ agonist baclofen ("BAC"). As a result, GABA$_{rho}$ is sometimes described as being a "BIC/BAC insensitive" receptor. In addition, GABA$_{rho}$ receptors are largely insensitive to steroids which modulate the activity of GABA receptors in both brain and retinal tissue.

For further details concerning the expression and responsiveness of GABA$_{rho}$, to various pharmacological agents, those skilled in the art may want to refer to Polenzani, et al., *Proc. Natl. Acad. Sci. USA*, 88:4318–4322, 1991; Woodward, et al., *Mol. Pharmac.*, 41:89–103, 1992; Woodward, et al., *Mol. Pharmac.*, 42:165–173, 1992; and, Woodward, et al., *Mol. Pharmacol.*, 43: 609–625, 1993, the disclosures of which are incorporated herein for the purpose of providing further background information regarding GABA$_{rho}$.

Generally, because GABA$_{rho}$ is highly expressed in retinal tissue as compared to GABA$_A$ and GABA$_B$, GABA$_{rho}$ receptors are likely to play a significant role in visual processing. Ligands which inhibit or enhance the responsiveness of GABA$_{rho}$ receptors to GABA would, therefore, be reasonably expected to depress or enhance processing of visual stimuli in visual pathways. Further, because GABA$_{rho}$ receptors appear to respond differently to ligands which affect conventional GABA receptors, ligands which selectively or preferentially bind GABA$_{rho}$ receptors may have little adverse affect on conventional GABA receptors.

Therefore, not only may ligands which selectively impact GABA$_{rho}$ receptors have beneficial therapeutic properties, such ligands would also be useful for research purposes, such as probing the function of GABA$_{rho}$ in vivo, identifying which structural subunits of the receptor render its responsiveness different from that of conventional GABA receptors, and identifying ligands which stimulate specific responses by conventional GABA receptors that are activated or inhibited by presently known ligands for conventional GABA receptors. To date, however, ligands which selectively or preferentially bind GABA$_{rho}$ receptors have not been identified.

Oocytes of the frog *Xenopus laevis* are used extensively in the field of molecular neurobiology as an expression system for mammalian neurotransmitter receptors using native poly (A)$^+$ RNA or RNA transcribed in vitro from cloned complementary DNA molecules (i.e., cDNA). A variety of neurotransmitter binding molecules such as G-protein coupled receptors (e.g., GABA$_B$), ligand-gated receptor/channel complexes (e.g., GABA$_A$), and voltage-gated channels have been expressed from Xenopus oocytes (for review, see Miledi, et al., *Fidia Res. Found.: Neuroscience Award Lectures*, Raven Press, 1989, at pp. 57–89). Generally, receptors and channels expressed in Xenopus oocytes retain their binding capacity for, responsiveness to, ligands which they respond to in vivo (see, e.g., Woodward, et al., *Mol. Pharmacol.*, 41:1107–1115, 1992 [GABA$_A$]; Woodward, et al., *Mol. Pharmacol.*, 42:165–173, 1992 [GABA$_{rho}$]; Woodward, et al., *Mol. Pharmacol.*, 41:89–103, 1992 [GABA$_A$ and GABA$_{rho}$]; and, Barnard, et al., *Neuropharmacology*, 26:837–844, 1987 [GABA$_A$]).

SUMMARY OF THE INVENTION

The present invention is directed toward novel tetrahydropyridyl phosphinic acid compounds with GABA$_{ergic}$ properties and to their use for alleviation of stress, for therapeutic applications in diseases related to the GABAergic neuronal system, and for modulating the responsiveness of mammalian $GABA_{rho}$ receptors.

These compounds have utility as modulators of the excitability of the central nervous system as mediated by their ability to specifically act on closed-channel binding sites of $GABA_{rho}$ receptors. Therefore, this invention is directed at methods, compounds and compositions of such compounds for use in the treatment of disorders associated with excitability of the central nervous system.

DETAILED DESCRIPTION OF THE INVENTION

I. Identification and Synthesis of the Hybrid Ligands of the Invention

The present invention provides a family of GABA receptor antagonists that are selective for $GABA_{rho}$ receptors but have little affinity for either $GABA_A$ or $GABA_B$ receptors. The molecular structure of the $GABA_{rho}$ receptor antagonists of this invention combines the amino substituted heterocyclic ring of the $GABA_A$ agonist with the substituted phosphinic acid of $GABA_B$ receptor agonists.

Electrical recording techniques and the Xenopus oocyte expression system were used to determine the sensitivity of a variety of commonly used $GABA_A$ and $GABA_B$ receptor ligands to $GABA_{rho}$ receptors expressed by bovine retina RNA. The results of these studies revealed the pharmacological profile of the bovine $GABA_{rho}$ receptors and suggested a strategy for designing drugs with enhanced likelihood of selective interaction with the $GABA_{rho}$ receptor subtype, without overt effects at other types of GABA receptors.

First it was discovered that $GABA_A$ receptor agonists, such as isoguvacine, isonipecotic acid and 4,5,6,7-tetrahydroisoxazolo-[5,4-c]-pyridin-3-ol (THIP) act on $GABA_{rho}$ receptors either as weak partial agonists or as competitive antagonists. The predominantly inhibitory effects at $GABA_{rho}$ receptors indicates that this class of GABA analogues, where the amino group has been incorporated into a heterocyclic ring, is tolerated by closed-channel binding sites on $GABA_{rho}$ receptors, but is either inactive, or only weakly active, in promoting channel gating. Previous studies had shown that these types of ligand were effectively inactive at $GABA_B$ receptors (see, e.g., Hill, et al. *Nature*, 290:149–152, 1981; and Krogsgaard-Larsen, et al., *Benzodiazepene/GABA Receptors and Chloride Channels: Structural and Functional Properties*, (Alan R. Liss, ed., 1986), at pp 73–95).

In addition, it was found that the $GABA_B$ receptor agonist 3-aminopropyl(methyl-)phosphinic acid is a surprisingly potent competitive antagonist at $GABA_{rho}$ receptors ($K_i$=0.8 μM), whereas this ligand has no detectable effects on $GABA_A$ receptors expressed either by rat brain mRNA or by bovine retina mRNA. When a methylphosphinic acid substituent was used to replace the carboxyl group of GABA in this compound, affects at $GABA_A$ receptors were prohibited, but relatively strong interactions at closed channel binding sites on $GABA_{rho}$ receptors were detected.

Figure 1:
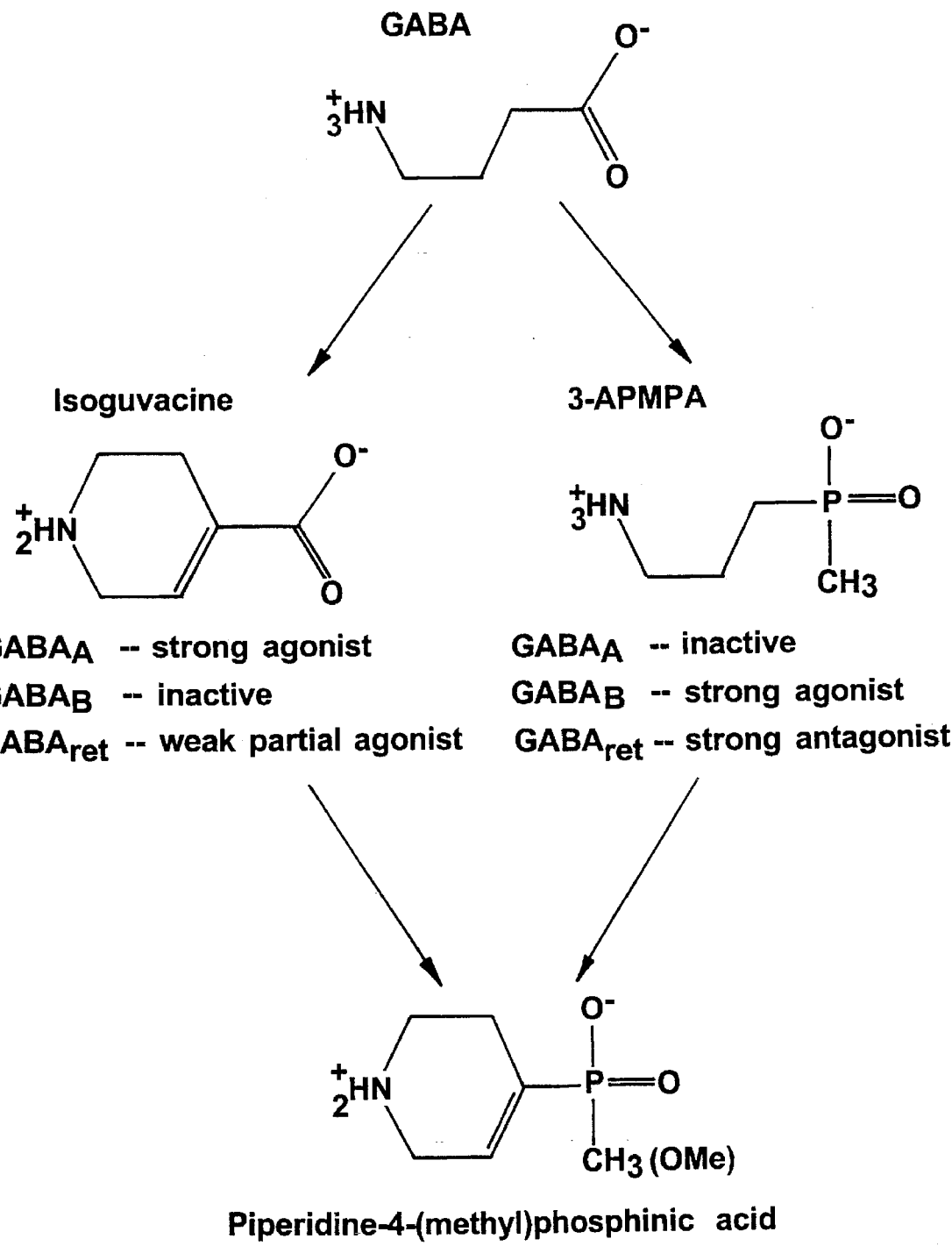
FIG. 1 is a schematic diagram showing the relation between the structure of GABA and the hybrid ligands that bind to the $GABA_{rho}$ receptor of this invention.

As shown in FIG. 1, based on these two observations, the selective $GABA_{rho}$ receptor antagonists of this invention incorporate both types of modifications to the GABA molecule. The amino group of GABA is incorporated into a heterocyclic ring and the carboxyl group of GABA is substituted by a phosphinic or phosphonic acid. These hybrid ligands are tolerated by closed-channel binding sites on $GABA_{rho}$ receptors, where they can act as competitive antagonists, but are substantially less potent, or wholly inactive at both $GABA_A$ receptors and $GABA_B$ receptors. Interactions of the hybrid ligand with $GABA_A$ receptors would be prohibited by the phosphinic acid substituent, and interactions with $GABA_B$ receptors would be prohibited by incorporating the amino group into a heterocyclic ring.

It will be appreciated by those of ordinary skill in the art on reviewing FIG. 1 that other starting ligands may be used to form the hybrid ligands of the invention. Specifically, pyridine and piperidine agonists of $GABA_A$ receptors other than those referred to above may be chemically joined to phosphinic and/or phosphonic agonists of $GABA_B$ receptors other than those referred to above by substitution of the latter at a carboxyl group of the former to form hybrid ligands. Such hybrid ligands will be considered to the within the scope of this invention as long as they possess the following functional characteristics:

1. the pyridine or piperidine or other charged ammonium starting ligand is a $GABA_A$ receptor agonist that is inactive at $GABA_B$ receptors, and either a weak or partial agonist of, or inactive at, $GABA_{rho}$ receptors;
2. the phosphinic or phosphonic acid starting ligand is inactive at $GABA_A$ receptors, but an agonist of $GABA_B$ receptors and an antagonist of $GABA_{rho}$ receptors; and,
3. the resulting hybrid ligand is active only at $GABA_{rho}$ receptors and is antagonistic vis-a-vis the response of $GABA_{rho}$ receptors to GABA.

Examples of starting ligands which would be expected (based on their known activity at GABA receptors and structure) to fit the aforementioned criteria are ZAPA analogues which possess a guanidine function at one end but no heterocyclic ring structure, and dihydro-pyridines or piperidines (i.e., dihydro-analogues of the tetrahydro- starting ligands identified in Scheme I [described infra], such as isonipecolic acid).

Following the logic of the above criteria and the approach illustrated in FIG. 1, suitable approaches to the synthesis of the hybrid ligands of the invention is to either incorporate the amino group of $GABA_A$ receptor ligands into a heterocyclic ring or to make an appropriate amino group substitution. For example, the unsaturated or saturated piperidine rings of isoguavacine, isonipecotic acid, and P-4-S seem to prohibit interactions with $GABA_B$ receptors (see, e.g., Hill, et al, *Nature*, 290:149–152, 1981; and, Bowery, et al., *Br.J. Pharmacol*, 78:191–206, 1983). In contrast, closed channel binding sites on the $GABA_{rho}$ receptors appear to tolerate this type of structural modification, albeit with some reduction in affinity with respect to GABA (see, re $GABA_{rho}$ receptor tolerance of unsaturated and saturated piperidine rings of isoguavacine, Miledi, et al., *Mol.Pharmacol*, 43: 609–625, 1993, the disclosure of which is incorporated herein for purposes of reference regarding the activity of certain known GABA receptor ligands).

Hence, a compound such as piperidine-4-(methyl) phosphinic acid, preferably unsaturated analogues thereof, could be reasonably expected to retain activity as competitive antagonists at $GABA_{rho}$ receptors. This reasoning also suggests that it would be reasonable to expect that the methylphosphinic acid analogues of ZAPA (substituting the isothiouronium moiety of ZAPA for the amino group of GABA) would serve as competitive antagonists for $GABA_{rho}$ receptors. Thus, the invention encompasses hybrid ligands having the formula (1):

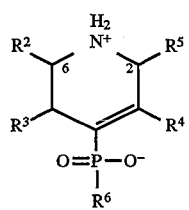

wherein $R^2$, $R^3$, $R^4$ and $R^5$ are independently selected from the group consisting of hydrogen, branched or straight chain alkyl, aryl, and heterocyclic substituents having between 1 and 20 carbon atoms; $R^6$ is selected from the group consisting of aryl and branched or straight chain alkyl and alkoxy substituents, and n is 1, 2, or 3;

as well as hybrid ligands having the formula (2):

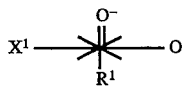

wherein $R^1$ is not present or is selected from the group consisting of hydrogen, oxygen, branched or straight chain alkyl, aryl having between 1 and 20 carbon atoms, X is a sulfonic moiety (S), a phosphonic or phosphinic moiety (P) or C, and X' is a saturated or unsaturated heterocyclic substituent or Y where Y is O, S or C; provided that where Y is present, it is bonded to Z, where Z is guanadinium or other related cationic functional group. In this context, "related" refers to groups which, though structurally not identical to guanadium, possess the same function vis-a-vis the criteria set forth above. Those of oridinary skill in the art will know of such equivalent groups, or can identify them without undue experimentation.

Preferred hybrid ligands useful as $GABA_{rho}$ receptor antagonists are the 4-, 3- or 6- phosphinic acid derivatives of tetrahydropyridines. Especially preferred is 1,2,5,6-tetrahydropyridin-4-alkylphosphinic acids (TPMPA and TPEPA). A general scheme for synthesis of 4-phosphinic acid derivatives of 1,2,5,6,-tetrahydropyridine is outlined in Scheme I below. Using the information provided herein, those of ordinary skill in the art will know, or can readily ascertain without undue experimentation, methods for determining whether the activity of other starting ligands and hybrid ligands meets the aforementioned criteria. Examples of such methods are described in the Examples provided in this disclosure as well as in the art; e.g., the publications identified in the background section, supra, of this disclosure.

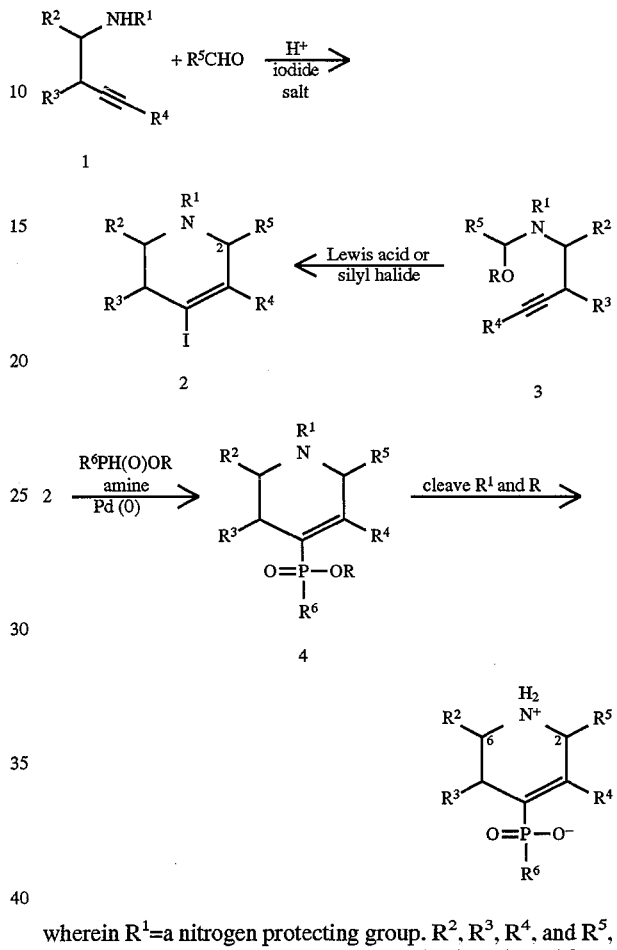

wherein $R^1$=a nitrogen protecting group. $R^2$, $R^3$, $R^4$, and $R^5$, are most preferably hydrogen, but can also be selected from alkyl, aryl, or an heterocyclic substituent containing from about 1 to 20 carbon atoms, preferably 1 to about 10 carbon atoms. $R^6$ is selected from alkyl, aryl or alkoxy substituent containing from about 1 to 10 carbon atoms.

Examples of nitrogen protecting groups are carbamates (such as 2-(trimethylsilyl), ethoxycarbonyl, tert-butoxycarbonyl and trichloroacetyl), 10 mer alkyl groups, arylalkyl groups (such as benzyl or 4-methyloxybenzyl), and sulfonyl groups (such as tosyl).

Although alternative methods may be used, the novel compounds of the invention are preferably prepared according to Scheme I from homopropargylamines and aldehydes. The conversion of Compound 1 to Compound 2 was reported earlier (L. E. Overman, et al., *J. Am. Chem. Soc.*, 110:612, 5934, 1988). The conversion of Compound 2 to Compound 4 is conceptually related, yet distinct from, the preparation of phosphinic acid-substituted steroids and tetrahydropyridines from ketones as disclosed in European patent application EP 375349 (see also D. A. Holt, et al, *Chem Abstr.*, 114(5):43308W and *Tetrahedron Lett.* 30:5393, 1989). Unless otherwise specified herein, including the claims, reference to the compounds of the invention, as discussed above is intended to include all isomers, whether separated or mixtures thereof.

A compound according to Scheme I wherein the nitrogen of the pyridine constituent is substituted with an alkyl containing from 1 to about 10 carbon atoms or an arylalkyl group can be obtained from the appropriate N substituted 4-iodo-1,2,5,6-tetrahydropyridine by omitting the choloroformate dealkylation step from the sequence in Scheme I.

A general scheme for synthesis of 3-phosphinic acid derivatives of tetrahydroazepine is presented in Scheme II below

SCHEME II

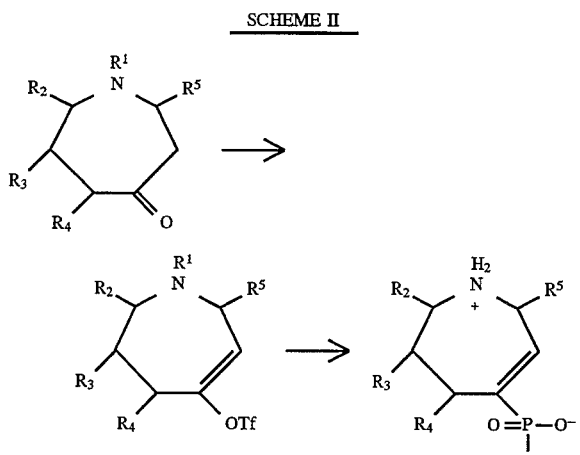

wherein $R^1$ is a nitrogen protecting group, and $R^2$, $R^3$, $R^4$ and $R^5$ are most preferably hydrogen, but can also be selected from alkyl aryl, or an heterocyclic substituent containing from about 1 to 20 carbon atoms, preferably 1 to about 10 carbon atoms. $R^6$ is selected from alkyl, aryl or alkoxy substituent containing from about 1 to 10 carbon atoms.

A general scheme for synthesis of 4-phosphinic acid derivatives of a pyrrole substituent is presented in Scheme III below:

SCHEME III

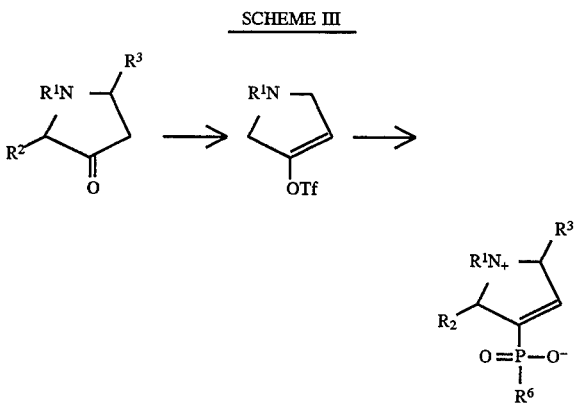

wherein $R^1$ is a nitrogen protecting group, and $R^2$, $R^3$ and $R^5$ are most preferably hydrogen, but can also be selected from alkyl, aryl, or an heterocyclic substituent containing from about 1 to 20 carbon atoms, preferably 1 to about 10 carbon atoms. $R^6$ is selected from alkyl, aryl or alkoxy substituent containing from about 1 to 10 carbon atoms.

The compounds of Schemes II and III are available from N-benzyl-3-azepinone or N-benzyl-3-pyrrolidinone (readily prepared from commercially available 3-pyrrolidinol) along the lines described with respect to Scheme I since enol triflates can be employed also in palladium-catalyzed cross coupling with HP(O)X nucleophiles (see, e.g., Hirao, et al., *Tetrahedron Lett.*, 21:3595, 1980; and, Holt, et al. *Tetrahe-*

*dron Lett.*, 30:5393, 1989). Regioselection in the enol triflation step will likely not be high, requiring chromatographic separation of isomers.

Alternatively 6-phosphinic acid derivatives of cyclohexenyl amines can be obtained as in Scheme IV below.

SCHEME IV

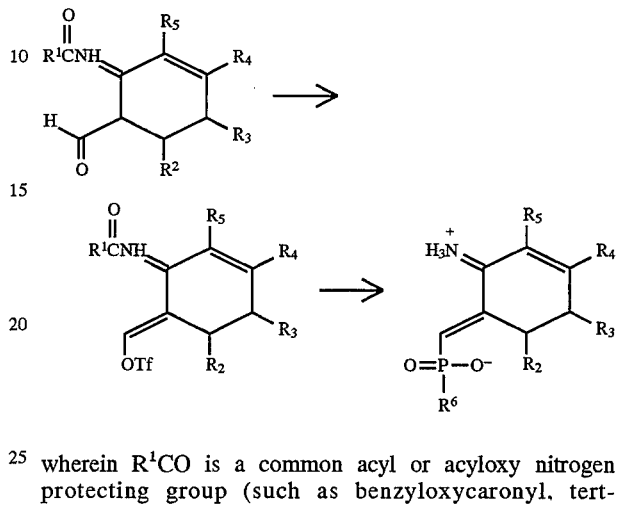

wherein $R^1CO$ is a common acyl or acyloxy nitrogen protecting group (such as benzyloxycaronyl, tert-butoxycarbonyl and trichloroacetyl), and $R^2$, $R^3$, $R^4$ and $R^5$ are most preferably hydrogen, but can also be selected from alkyl, aryl, or an heterocyclic substituent containing from about 1 to 20 carbon atoms, preferably 1 to about 10 carbon atoms. $R^6$ is selected from alkyl, aryl or alkoxy substituent containing from about 1 to 10 carbon atoms.

The compounds of Scheme IV position the amine and phosphinic acid functional groups by an "external" six-membered ring in an orientation similar to that found in TPMPA. The readily available Diels-Alder adduct (Jessup, et al., *Organic Syntheses*, 59:1, 1979; and, Overman, *Accounts of Chemical Research*, 13:210, 1980) serves as a precursor of enol triflate, and, thus of the desired compound. Both enantiomers are prepared (usually due to asymmetric catalysis of the initial Diels-Alder reaction) and can be used to define the stereochemical aspects of the $GABA_{rho}$ receptor.

II. Pharmaceutical Compositions of the Invention

The pharmaceutical compositions of this invention can be prepared in conventional dosage unit forms by incorporating a compound of the invention or a mixture of such compounds, with a nontoxic pharmaceutical carrier according to accepted procedures in a nontoxic amount sufficient to produce the desired pharmacodynamic activity in a subject, animal or human.

Dosages of the pharmaceutical compositions of the invention can vary from about 10 units/m² to 20,000 units/m², preferably from about 5000 to 6000 units/m², in one or more dose administrations weekly, for one or several days. This quantity depends on the specific biological activity desired and the condition of the patient. The most desirable object of the composition and methods is in the treatment of anxiety, muscle tension and depression common with patients suffering from central nervous system abnormalities or modulation of mammalian visual processing. A dosage which achieves one or more of these results will be considered a "pharmaceutically effective" dosage.

The pharmaceutical carrier employed may be, for example, either a solid, liquid, or time release (see, standard reference *Remington's Pharmaceutical Sciences* which is incorporated herein by reference to illustrate knowledge in the art concerning suitable pharmacuetical carriers). Exemplary of solid carriers are lactose, terra alba, sucrose, talc, gelatin, agar, pectin, acacia, magnesium stearate, stearic acid, microcrystalline cellulose, polymer hydrogels and the like. Exemplary of liquid carriers are syrup, peanut oil, and olive oil and the like emulsions. Similarly, the carrier or diluent may include any time delay material well known to the art, such as glyceryl monostearate or glyceryl distearate alone or with a wax, microcapsules, microspheres, liposomes, and hydrogels.

A wide variety of pharmaceutical forms can be employed. Thus, when using a solid carrier the preparation can be tableted (however, the oral route of administration should be avoided due to first pass metabolic degradation), placed in a hard gelatin capsule in powder or pellet form, or in the form of a troche, lozenge or suppository. When using a liquid carrier the preparation can be in the form of a liquid, such as an ampule, or as an aqueous or nonaqueous liquid suspension. Liquid dosage forms also need pharmaceutically acceptable preservatives and the like. In addition, because of the low doses which will be required as based on the in vitro data disclosed herein, topical administration via timed release skin patches is also a suitable pharmaceutical form.

The method of producing anxiolytic or anti-excitatory activity, in accordance with this invention, comprises administering internally to a subject in need of such activity a compound of the invention, usually prepared in a composition as described above with a pharmaceutical carrier, in a nontoxic amount sufficient to produce said activity as described above.

III. Methods for Screening Hybrid Ligand and $GABA_{rho}$ Receptor Activity

For convenience and relevance to human receptor function, potential hybrid ligands will preferably be screened for binding to $GABA_{rho}$ receptors expressed by Xenopus oocytes as described in Example III. Those of skill in the art will recognize, however, that ligand binding to $GABA_{rho}$ receptors may also be characterized by determination of other parameters, such as binding kinetics and affinity.

It will be appreciated by those of skill in the art that in vivo use of the hybrid ligands of the invention to modulate $GABA_{rho}$ receptor responses in brain tissue will depend on the ability of such compounds to cross the blood/brain barrier. That ability may, however, be confirmed by administration of individual compounds in a suitable animal model, such as the murine model. Detection of the hybrid ligands of the invention in the brain tissue may be made by means known to those of skill in the art.

For example, determination of whether a particular hybrid ligand of the invention will cross the blood/brain barrier can be made by one of ordinary skill in the art without undue experimentation by labelling the hybrid ligand with a label detectable in vivo, such as a radioisotope or paramagnetic isotope, and administering the detectably labelled agent to suitable individuals of an animal model for in vivo imaging of any such agent in the animal's brain tissue. An important factor in selecting a radioisotope for in vivo imaging is that the half-life of the radioisotope be long enough so that it is still detectable at the time of maximum uptake by the target, but short enough so that deleterious radiation with respect to the host is minimized. Suitable radioisotopes include $^{125}$I, $^{99m}$Tc, $^{111}$In, $^{97}$Ru, $^{67}$Ga, $^{68}$Ga, $^{72}$As, $^{89}$Zr, $^{90}$Y, and $^{201}$Ti. Of these, a preferred radioisotope for in vivo use is reduced [$^{99m}$Tc] pertechenetate for its relatively low toxicity in mammals. However, for any in vitro use, $^{125}$Iodide ($^{125}$I) would be preferred for ease of detection.

The hybrid ligands of the invention may also be labelled with a paramagnetic isotope for purposes of in vivo detection as in magnetic resonance imaging (MRI) or electron spin resonance (ESR). In general, any conventional method for visualizing detectable labels in vivo can be utilized. Usually gamma and positron emitting radioisotopes are used for camera imaging and paramagnetic isotopes for MRI. Elements which are particularly useful in such techniques also include $^{157}$Gd, $^{55}$Mn, $^{162}$Dy, $^{52}$Cr and $^{56}$Fe.

It will be further appreciated by those of ordinary skill in the art that labelled hybrid ligands of the invention will be useful in vivo and in vitro in research to identify, quantitate, and study the activity and kinetics of $GABA_{rho}$ receptors.

The following examples illustrate the manner in which the invention can be practiced. It is understood, however, that the examples are for the purpose of illustration and the invention is not to be regarded as limited to any of the specific materials or conditions therein.

EXAMPLE I

Synthesis of Hybrid Ligands and Intermediates

A. Synthesis of N-benzyl-4-iodo-1,2,5,6-tetrahydropyridine Compound 2)

A solution of N-benzyl-3-butyn-1-amine (Compound 1) (1.03 g, 5.9 mmol), (L. E. Overman, et al., *J. Am. Chem. Soc.*, 110:612, 1988; H. J. Arnold, et al., *Org. Synth.*, 70:111, 1991); camphorsulfonic acid (1.56 g, 6.7 mmol), NaI (4.5 g, 30 mmol); and 37% w/w aqueous formalin (9 mL, 120 mmol) and $H_2O$ (25 mL) was heated at reflux for 1 h. The resulting solution was cooled to room temperature and partitioned between $CH_2Cl_2$ (3×20 mL) and 1N KOH (20 mL). The aqueous layer was extracted with $CH_2Cl_2$ (20 mL) and the combined organic layers were dried ($MgSO_4$) and concentrated. Purification of the residue by column chromatography (15–10:1 hexane-ether, 5% $Et_3N$) gave 1.44 g (81%) of 2 as a yellow oil, which rapidly darkened on standing: IR (film) 2780, 1545, 1384, 1341, 1054, 981, 729, 698 cm$^{-1}$; $^1$H NMR (300 MHz, CDCl$_3$) δ 7.20–7.40 (m, 5H), 6.26 (t, J=3.3 Hz, 1H), 3.56 (s, 2H), 3.02 (d, J=3.0 Hz, 2H), 2.61 (s, 4H); $^{13}$C NMR (75 MHz, CDCl$_3$) δ 137.8, 135.2, 129.1, 128.3, 127.2, 93.1, 62.2, 55.6, 51.6, 39.7; MS (CI) m/z 301 (9), 300(MH, 100), 174 (34); HRMS (CI) m/z 300.0251 (300.0254 calc'd for $C_{12}H_{15}NI$).

B. Synthesis of Methyl Hydrogen Methylphosphite (Compound 3a) and Methyl Hydrogen Ethylphosphite (Compound 3b)

These known reagents were prepared by the general procedure of K. A. Petrov, et al., *Zh. Obshch. Khim.*, 31:179, 1961). Methyldichlorophosphine is commercially available from Sterm (Newburyport, Mass.) and ethyldichlorophosphine is commercially available from Aldrich (Milwaukee, Wis.). To a solution of methyl or ethyl dichlorophosphine (35 mmol) in 25 mL of dry $Et_2O$ cooled to 0° C was added with stirring a solution of anhydrous MeOH (77 mmol), $Et_3N$ (35 mmol) and 25 mL of $Et_2O$. The reaction mixture then was heated for 30–40 minutes so that $Et_2O$ boiled gently. After cooling to room temperature, the reaction mixture was allowed to stand overnight to precipitate the amine hydrochloride. After filtration, the solvent was distilled from the filtrate and the residue was distilled to give the products compounds 3a and 3b (63 65%): bp. 66°–8° C./16 mmHg for 3a; 72°–74° C./14 mmHg for compound 3b.

C. Synthesis of N-benzyl-4-(methylmethyiphosphino)-1,2,5,6-tetrahydropyridine (Compound 4a)

Following related general procedures (T. Hirao, et al., "Palladium-catalyzed phosphorylation of alkenyl iodides or triflates," *Tetrahedron Lett.*, 21:3595, 1980; D. A. Holt, et al., *Tetrahedron Lett.*, 30:5393, 1989; M. A. Levy, et al., *Bioorganic Chem.*, 19:245, 1991), a mixture of compound 2 (449 mg, 1.5 mmol), methyl hydrogen methylphosphite (compound 3a) (202 mg, 2.1 mmol), 1,4-diazobicyclo[2.2.2]octane (DABCO, 512 mg, 4.6 mmol), Pd(PPh$_3$)$_4$ (52 mg, 0.045 mmol) and toluene (15 mL) was stirred under N$_2$ at 80°14 90° C. for 1 h. The reaction mixture was concentrated and the residue purified by column chromatography (CH$_2$Cl$_2$/hexane=5:3–2:1, containing 5% Et$_3$N) to give the methyl methylphosphinate (compound 4a) (212 mg, 53%) as a viscous oil: $^1$H NMR (300 MHz, CDCl$_3$) δ 7.20–7.40 (m, 5H), 6.67 (dd, J=19.2, 1.2 Hz, 1H), 3.58 (d, J=5.1 Hz, 3H), 3.55 (d, J=1.2 Hz, 2H), 3.01–3.22 (m, 2H), 2.47–2.68 (m, 2H), 2.22 (bs, 2H), 1.43 (dd, J=14.4, 0.6 Hz, 3H); $^{13}$C NMR (75 MHz, CDCl$_3$) δ 140.6 (d, J=8.6 Hz), 128.8, 128.2 (d, J=122 Hz), 128.1, 127.0, 62.2, 52.9 (d, J=14.0 Hz), 50.4 (d, J=4.5 Hz), 48.6 (d, J=9.3 Hz), 25.3 (d, J=9.4 Hz), 12.7 (d, J=100 Hz); IR (film) 2917, 1645, 1456, 1208, 1038, 894, 700 cm$^{-1}$; HRMS (Cl) m/z 266.1322 (266.1310 calc'd for C$_{14}$H$_{21}$NO$_2$P).

D. Synthesis of N-benzyl-4-(methylethylphosphino)-1,2,5,6-tetrahydropyridine (Compound 4b)

In a similar manner, a mixture of Compound 2(16.4 g, 55 mmol), methyl hydrogen ethylphosphite (Compound 3b) (8.4 g, 78 mmol), DABCO (18.8 g, 168 mmol), Pd(PPh$_3$)$_4$ (2.0 g, 1.7 mmol) and toluene (550 mL) was stirred under N$_2$ at 80°–90° C. for 1 h. The reaction mixture was concentrated and the residue purified by column chromatography (CH$_2$Cl$_2$/hexane=1:1–1.25:1, containing 5% Et$_3$N) to give the methyl ethylphosphinate (compound 4b) (5.16 g, 34%) as a viscous oil: $^1$H NMR (300 MHz, CDCl$_3$) δ 7.25–7.40 (m, 5H), 6.69 (dd, J=18.3, 1.5 Hz, 1H), 3.61 (d, J=10.8 Hz, 3H), 3.60 (s, 2H, CH$_2$Ph), 3.05–3.25 (m, 2H), 2.50–2.60 (m, 2H), 2.17–2.27 (m, 2H), 1.57–1.85 (m, 2H), 1.11 (dt, J=18.6, 7.8 Hz, 3H); $^{13}$C NMR (75 MHz, CDCl$_3$) δ 141.5 (d, J=6.8 Hz), 137.6, 129.0, 128.3, 127.3 (d, J=119 Hz), 127.2, 62.3, 53.1 (d, J=14.0 Hz), 50.7 (d, J=6.6 Hz), 48.8 (d, J=8.7 Hz), 25.7 (d, J=9.2 Hz), 19.8 (d, J=100 Hz), 5.5. (d, J=3.6 Hz); IR (film) 2946, 2918, 1643, 1457, 1210, 1049, 700 cm$^{-1}$; HRMS (Cl) m/z 280.1458 (280.1466 calc'd for C$_{15}$H$_{23}$NO$_2$P).

E. Synthesis of N-(trimethylsilylethyformyl)-4-(methylmethylphosphino)1,2,5,6-tetrahydropyridine (Compound 6a)

Following a general procedure, (A. L. Campbell, et al, *Tetrahedron Lett.*, 28:2331, 1987; C. Kim, et al., *Am. Chem. Soc.*, 115:30, 1993), a solution of 2-(trimethysilyl)ethyl chroroformate 5 (6.68 g, 37.0 mmol) (V. P. Kozyukov, et al., *Zh. Obshch. Khim.*, 38:1179, 1968) in dry toluene (10 mL) was added to a solution of Compound 4a (6.98 g, 26.4 mmol), which had been previously dried by azeotroping twice with toluene, in toluene (20 mL) at room temperature under N$_2$. The reaction mixture was stirred overnight at this temperature and then concentrated. The residue was purified by column chromatography (CH$_2$Cl$_2$/hexane=1:1–1.5:1, containing 5% Et$_3$N) to give the product compound 6a (6.39 g, 76%) as a viscose oil: IR (film) 2954, 1699, 1457, 1282, 1236, 1038 cm$^{-1}$; $^1$H NMR (300 MHz, CDCl$_3$) δ 6.73 (dd, J=19.2, 1.2 Hz, 1H), 4.18–4.25 (m, 2H), 4.07–4.17 (m, 2H), 3.62 (d, J=11.1 Hz, 3H), 3.47–3.68 (m, 2H), 2.21–2.30 (m, 2H), 1.48 (d, J=14.1 Hz, 3H), 0.97–1.06 (m, 2H), 0.04 (s, 9H); $^{13}$C NMR (75 MHz, CDCl$_3$) δ 155.4, 138.9 (d=4.4 Hz), 129.1 (d, J=124 Hz), 63.7, 50.6 (d, J=5.8 Hz), 43.9 (d, J=13.7 Hz), 39.6, 24.4 (d, J=6.8 Hz), 17.7, 12.7 (d, J=101 Hz), −1.6; HRMS (Cl) m/z 320.1431 (320.1447 calc'd for C$_{13}$H$_{27}$NO$_4$PSi).

F. Synthesis of N-(trimethylsilylethyforml)-(4-methylethylphosphino)-1,2,5,6-tetrahydropyridine (Compound 6b)

In a similar fashion, a solution of 2-(trimethysilyl)ethyl chroroformate 5 (3.90 g, 21.6 mmol) in toluene (2 mL) was added to a solution of 4b (4.30 g, 15.4 mmol) in toluene (8 mL) at room temperature under N$_2$. The reaction mixture was stirred overnight at this temperature and then concentrated. The residue was purified by column chromatography (CH$_2$Cl$_2$/hexane=1:2–1:1, containing 5% Et$_3$N) to give the product compound 6b (4.25 g, 83%) as a viscose oil: IR (film) 2973, 1699, 1436, 1238, 1207, 1043 cm$^{-1}$; $^1$H NMR (300 MHz, CDCl$_3$) δ 6.68 (d, J=18.3 Hz, 1H), 4.13–4.22 (m, 2H), 4.04–4.13 (m, 2H), 3.59 (d, J=18.0 Hz, 3H), 3.43–3.65 (m, 2H), 2.15–2.27(m, 2H), 1.55–1.85 (m, 2H), 1.08 (dt, J=18.6, 7.8 Hz, 3H), 0.94–1.05 (m, 2H), 0.00 (s, 9H); $^{13}$C NMR (75 MHz, CDCl$_3$) δ 155.5, 139.7 (d, J=5.9 Hz), 128.1 (d, J=118 Hz), 63.8, 50.8 (d, J=7.1 Hz), 44.0 (d, J=14.0 Hz), 39.6 (m), 24.7, 19.7 (d, J=100 Hz), 17.7, 5.5 (d=3.5 Hz), −1.5; HRMS (Cl) 333.1533 (M+ 333.1525 calc'd for C$_{14}$H$_{28}$NO$_4$PSi).

G. Synthesis of 1,2,5,6-tetrahydropyridine-4-methylphosphinate (Compound 7a)

A mixture of compound 6a (6.3 g, 19.8 mmol), 48% HBr (158 mL) and glacial CH$_3$COOH (158 mL) was heated at reflux (bath temperature 90°–100° C) for 1 day and concentrated. To this residue, toluene (20 mL) was added and the resulting mixture was concentrated (procedure repeated twice), and then saturated aqueous NH$_4$OH was added slowly until the solution was basic. This solution was concentrated, additional toluene (20 mL) was added and the solution again concentrated. The resulting residue was purified by ion exchange chromatography (Dowex 50W) to give the product compound 7a (2.96 g, 93%): Rf=0.52 (BuOH:CH$_3$COOH:pyridine:H$_2$O=6:6:3:5); $^1$H NMR (300 MHz, CD$_3$OD) δ 6.33 (d, J=17.1 Hz, 1H), 3.30 (t, J=1.4 Hz, 2H); $^{13}$C NMR (75 MHz, CD$_3$OD) δ 138.3 (d, J=121 Hz), 128.6 (d, J=8.2 Hz), 43.4 (d, J=13.9 Hz), 41.8 (d, J=8.4 Hz), 23.3 (d, J=9.8 Hz), 16.1 (d, J=97.8 Hz); HRMS (EI) m/z 161.0601 (161.0606 calc'd for C$_6$H$_{12}$NO$_2$P).

H. Synthesis of 1,2,5,6,-tetrahydropyridine-4-ethylphosphinate (Compound 7b)

In a similar manner, a mixture of 6b (4.25 g, 12.8 mmol), 48% HBr (102 mL) and glacial CH$_3$COOH (102 mL) was heated at reflux (heat-bath temperature 90°–100° C.) for 1 day and then concentrated. To this residue, toluene (20 mL) was added and the resulting mixture was concentrated (procedure repeated twice), and then saturated aqueous NH$_4$OH was added slowly until the solution was basic. This solution was concentrated, additional toluene (20 mL) was added and the solution again concentrated. The resulting residue was purified by ion exchange column (Dowex 50W) to give the product compound 7b (1.99 g, 89%): Rf=0.52 (BuOH:CH$_3$COOH:pyridine:H$_2$O=6:6:3:5): $^1$H NMR (300 MHz, CD$_3$OD) δ 6.34 (d, J=17.1 Hz, 1H), 3.58 (t, J=2.4 Hz, 2H), 3.11 (t, J=5.7 Hz, 2H), 2.40 (t, J=2.1 Hz, 2H), 1.50 (qd, J=15.0, 7.5 Hz, 2H), 1.03 (dt, J=17.4, 7.7 Hz, 3H); $^{13}$C NMR (75 MHz, CD$_3$OD) δ 136.7 (d, J=117 Hz), 131.3 (d, J=6.5 Hz), 44.0 (d, J=13.0 Hz), 42.1 (d, J=8.1 Hz), 24.3 (d, J=9.4 Hz), 23.4 (d, d=97.9 Hz), 7.3 (d, J=3.8 Hz); HRMS (EI) m/z 175.0759 (175.0762 calc'd for C$_7$H$_{14}$NO$_2$P).

EXAMPLE II

Purification of Compounds 7a and 7b by Ion-Exchange Chromotagraphy

The cation-exchanger DOWEX 50W (ca 50 g) (a trademarked product of Fulka Corp., Ronkonkoma, N.Y.), was washed with 1N HCl (ca 150 mL, 5–6 times until the supernatant liquid is colorless). After packing this resin, the column was washed with ca 2 L of distilled water until the eluent was neutral to pH paper. A solution of crude compound 7a or 7b (ca 500 mg) in distilled water (ca 20 mL) then was applied to this column, which was eluted with distilled water (500 mL) and then with a mixture of saturated $NH_4OH$ and distilled water (1:50–1:20). The first strongly acid ninhydrin-negative fractions were rejected. By the evaporation of neutral or weakly basic, ninhydrin-positive fractions, the pure tetrahydropyridyl phosphinic acid was isolated.

EXAMPLE III

Figure 2:
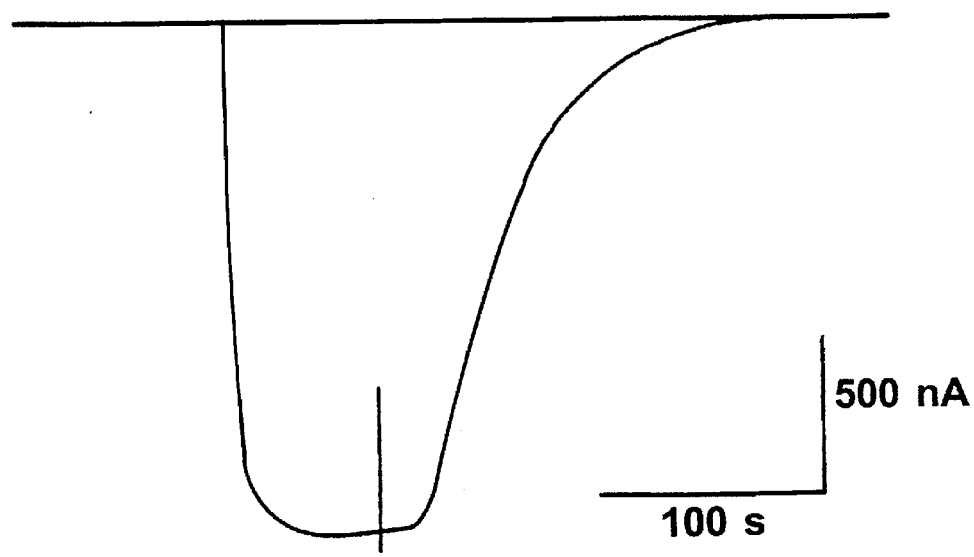
FIG. 2 is a graph showing membrane currents elicited $10^{-5}$ M GABA in an oocyte expressing cloned $GABA_{rho}$ receptors and those generated when the same concentration of GABA was administered together with $8 \times 10^{-5}$ M of 1,2,5,6-tetrahydropyridine-4-methylphosphinic acid (TPMPA).
Figure 3:
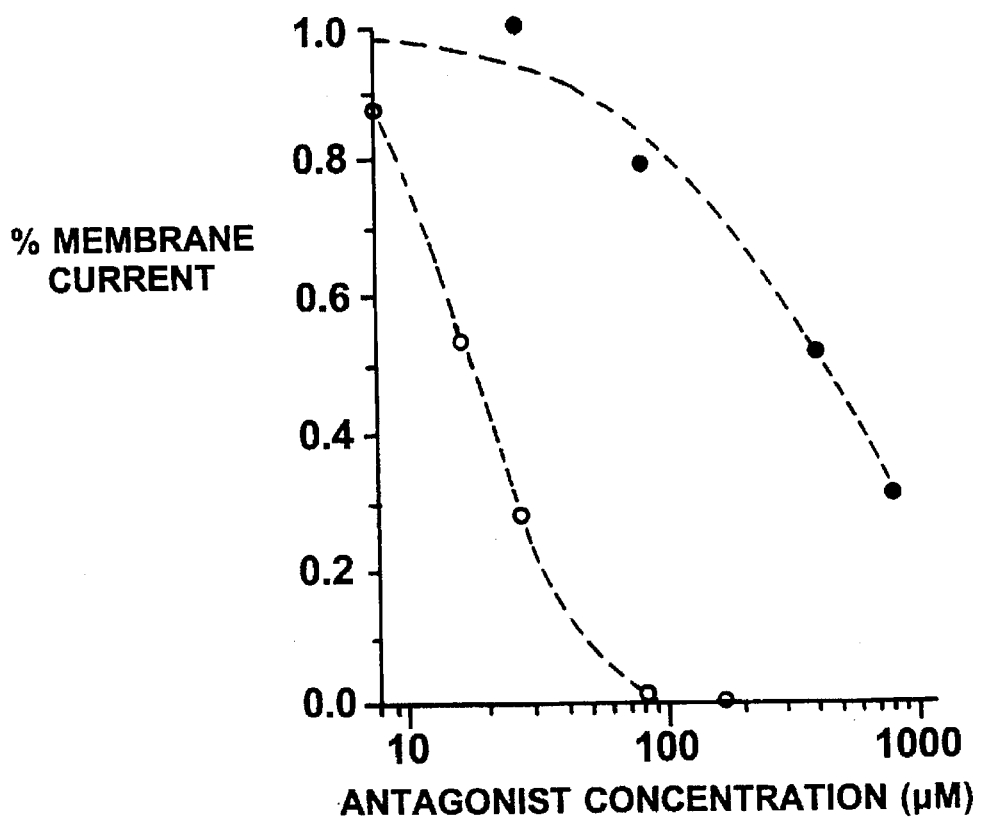
FIG. 3 is a graph comparing antagonistic action of TPMPA on GABA ($10^{-5}$) in an oocyte expressing cloned $GABA_{rho}$ receptors $_{(rho)}$ and in another oocyte expressing chick brain $GABA_A$ receptors (o).

To test the new compounds synthesized, Xenopus oocytes were injected with the cloned GABA RNA and other oocytes were injected with native poly $(A)^+$ RNAs extracted from the rat cerebral cortex or spinal cord, bovine brain, rabbit brain, chick brain or optic lobe. As shown in FIG. 2, the membrane currents recorded from oocytes expressing cloned $GABA_{rho}$ receptors from application of GABA alone ($10^{-5}$ M) were compared with those generated when the same concentration of GABA was applied together with $8 \times 10^{-5}$ M of Compound 7a. At this concentration Compound 7a abolishes almost completely the response to GABA. FIG. 3 shows the antagonistic action at various concentrations of compound 7a (TPMPA) on GABA in an oocyte expressing cloned $GABA_{rho}$ receptors as compared with that in another oocyte expressing check brain $GABA_A$ receptors. The various concentrations of compound 7 were applied together with $10^{-5M}$ GABA. By contrast, currents elicited by activation of $GABA_A$ receptors were not greatly attenuated until quite high concentration were used.

These studies show that TPMPA is a potent and selective antagonist of $GABA_{rho}$ receptors expressed by either native bovine retina mRNA or cloned $GABA_{rho}$ receptor RNA and that the $GABA_A$ receptors expressed by native mRNAs from the brain of different animal species are differentially antagonized by TPMPA, although in all cases the blockage was less than that of $GABA_{rho}$ receptors.

Figure 4:
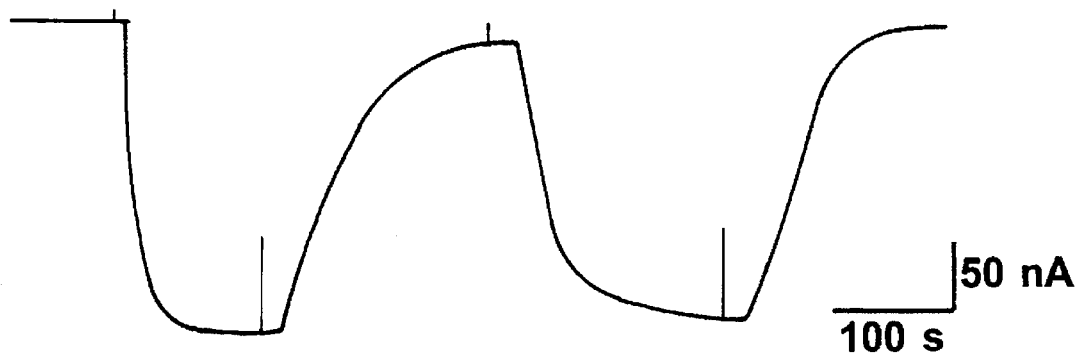
FIG. 4 is a graph showing consecutive membrane currents elicited by GABA ($3 \times 10^{-6}$ M) first alone, and then with the specified concentration of 1,2,5,6-tetrahydropyridine-4-ethylphosphinic acid (TPEPA).
Figure 5:
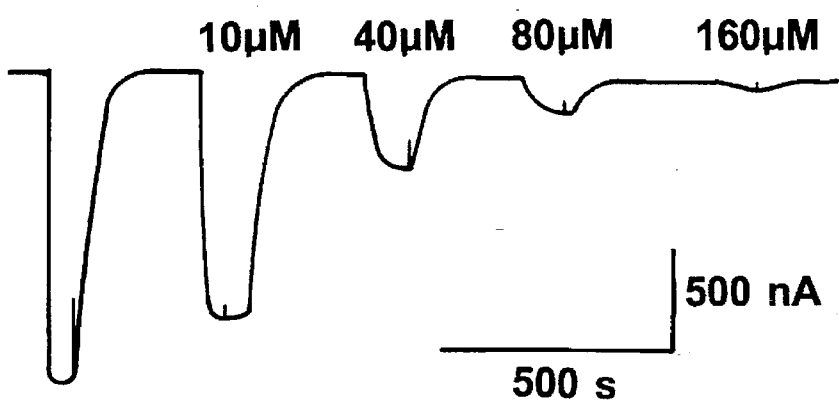
FIG. 5 is a graph showing consecutive membrane currents elicited by GABA ($3 \times 10^{-6}$M) first alone and then together with the specified concentration of TPEPA.

To study the time to onset of antagonistic action by TPMPA, a timed trial utilizing pulsed application of GABA ($10^{-5}$ M) and TPMPA ($8 \times 10^{-5}$ M) was begun. At the first marker pulse of 50 nA, GABA administration of GABA was begun. TPMPA was applied between the 2nd and 3rd markers, and normal Ringers solution (without GABA) was applied at the 4th marker pulse. As shown in FIG. 4, in all cases the antagonistic action of TPMPA was rapid in onset and the recovery was also rapid for cloned $GABA_{rho}$ receptors. As shown in FIG. 5, similar tests were conducted using varying concentrations of 1,2,5,6-tetrahydropyridine-4-ethylphosphinic acid (TPEPA) (compound 7b) to determine the onset and recovery time for cloned $GABA_{rho}$ receptors.

We claim:
1. A compound having the formula:

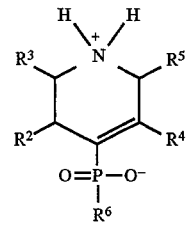

wherein each of $R^2$, $R^3$, $R^4$, and $R^5$ is hydrogen; and $R^6$ is selected from the group consisting of $C_{6-10}$ aryl, branched or straight chain $C_{-10}$ alkyl, and branched or straight chain $C_{1-10}$ alkoxy; or a pharmaceutically acceptable salt thereof.

2. The compound of claim 1 wherein $R^6$ is methyl.
3. The compound of claim 1 wherein $R^6$ is ethyl.
4. A composition comprising:
   a pharmaceutically acceptable carrier; and
   a pharmaceutically effective amount of a compound having the formula:

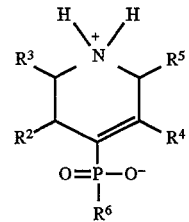

wherein each of $R^2$, $R^3$, $R^4$, and $R^5$ is hydrogen; and $R^6$ is selected from the group consisting of $C_{1-10}$ aryl, branched or straight chain $C_{1-10}$ alkyl, and branched or straight chain $C_{1-10}$ alkoxy; and pharmaceutically acceptable salts thereof.

5. The composition of claim 4 wherein $R^6$ is methyl.
6. The composition of claim 4 wherein $R^6$ is ethyl.
7. A method for modulating the responsiveness of mammalian $GABA_{rho}$ receptors comprising exposing mammalian $GABA_{rho}$ receptors to an effective receptor-modulating amount of a compound having the formula:

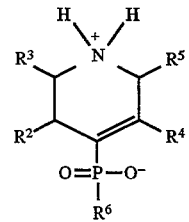

wherein each of $R^2$, $R^3$, $R^4$, and $R^5$ is hydrogen; and $R^6$ is selected from the group consisting of $C_{6-10}$ aryl, branched or straight chain $C_{1-10}$ alkyl, and branched or straight chain $C_{1-10}$ alkoxy; or a pharmaceutically acceptable salt thereof.

8. The method of claim 7 wherein $R^6$ is methyl.
9. The method of claim 8 wherein $R^6$ is ethyl.

* * * * *